United States Patent [19]
Johnson et al.

[11] Patent Number: 5,180,504

[45] Date of Patent: Jan. 19, 1993

[54] SYSTEMS AND METHODS FOR REMOVING UNDESIRED MATTER FROM BLOOD CELLS

[75] Inventors: Kenneth M. Johnson, Lindenhurst; Samira E. Monaghan, Lake Zurich, both of Ill.

[73] Assignee: Baxter International Inc., Deerfield, Ill.

[21] Appl. No.: 704,077

[22] Filed: May 22, 1991

[51] Int. Cl.$^5$ ............................................. B01D 37/00
[52] U.S. Cl. ................................... 210/767; 210/233; 210/257.1; 210/420; 210/806; 422/41; 422/44; 435/2; 604/406; 604/409; 604/410
[58] Field of Search .............. 210/767, 749, 806, 787, 210/800, 233, 257.1, 196, 234, 420; 422/41, 44; 604/406, 409, 410; 435/2

[56] References Cited

U.S. PATENT DOCUMENTS

| | | | |
|---|---|---|---|
| 4,157,723 | 6/1979 | Granzow et al. | 141/1 |
| 4,265,280 | 5/1981 | Ammann et al. | 141/98 |
| 4,267,269 | 5/1981 | Grode et al. | 435/2 |
| 4,412,835 | 11/1983 | Spencer | 604/29 |
| 4,596,657 | 6/1986 | Wisdom | 210/257.1 |
| 4,767,541 | 8/1988 | Wisdom | 210/806 |
| 4,810,378 | 3/1989 | Carmen et al. | 210/257.1 |
| 4,855,063 | 8/1989 | Carmen et al. | 210/806 |
| 4,919,823 | 4/1990 | Wisdom | 210/749 |
| 4,943,287 | 7/1990 | Carmen | 604/408 |
| 4,997,577 | 3/1991 | Stewart | 210/767 |

Primary Examiner—Robert A. Dawson
Assistant Examiner—Sun Uk Kim
Attorney, Agent, or Firm—Bradford R. L. Price; Daniel D. Ryan; Paul C. Flattery

[57] ABSTRACT

Systems and methods for collecting blood substantially free of undesired matter assure that accurate cross-matching and typing of cellular blood components can be done prior to transfusion, even though the cellular components are collected and stored in different containers. The blood containing the undesired matter is collected in a blood collection container. The blood collection container includes a tube that is sealed for retaining samples of the collected blood for later analysis. The collected blood is conveyed out of the blood collection container for removal of undesired matter. The blood substantially free of the undesired matter is collected in a separate transfer container for storage. The distal end of the sealed tube containing the blood samples is attached to the transfer container, while the other end of the sealed tube is disconnected from the original blood collection container. This leaves the sealed tube and, with it, the retained blood sample, attached only to the transfer container, which now holds blood substantially free of undesired matter. Using the systems and methods, direct traceability can be assured between red blood cells made substantially free of white blood cells for transfusion and the donor from whom the red blood cells were obtained.

13 Claims, 4 Drawing Sheets

RADIANT ENERGY SOURCE

SYSTEMS AND METHODS FOR REMOVING UNDESIRED MATTER FROM BLOOD CELLS

FIELD OF THE INVENTION

The invention generally relates to blood collection and processing systems and methods. In a more particular sense, the invention relates to systems and methods for removing white blood cells from red blood cells prior to transfusion or long term storage.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Systems composed of multiple, interconnected plastic bags have met widespread use and acceptance in the collection, processing and storage of these blood components. In the United States, these multiple blood bag systems are subject to regulation by the government. For example, the plastic materials from which the bags and tubing are made must be approved by the government. In addition, the maximum storage periods for the blood components collected in these systems are prescribed by regulation.

In the United States, whole blood components collected in a nonsterile, or "open", system (i.e. one that is open to communication with the atmosphere) must, under governmental regulations, be transfused within twenty-four hours. However, when whole blood components are collected in a sterile, or "closed", system (i.e., one that is closed to communication with the atmosphere), the red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

Before transfusing cellular blood components like red blood cells, it is important assure that the blood type of the recipient matches the blood type of the donor. For this reason, conventional blood collection procedures collect several small aliquots or samples of the donated whole blood for use in crossmatching and typing the donor's blood prior to transfusion.

Typically, as FIG. 1 shows, the samples are obtained after collecting the whole blood, by expressing a small amount of the collected whole blood (now mixed with an anticoagulant) from the primary collection bag 2 back into donor tube 4 that is attached to the bag 2. In this process, the phlebotomy needle 6 is removed, and sealed pockets 8 are formed along the length of the donor tube 4, where the samples of the donor's anticoagulated whole blood are retained. The pockets 8 are formed using a conventional heat sealing device (for example, the Hematron ® dielectric sealer sold by Baxter Healthcare Corporation), which forms hermetic, snap-apart seals (designated "S" in FIG. 1) spaced apart along the length of the donor tube 4.

After the whole blood samples are collected in the donor tube 4, conventionally procedures then centrifugally process the whole blood within the primary bag 2 to separate it into red blood cells and platelet-rich plasma. The platelet-rich plasma is expressed from the primary bag 2 into an integrally attached transfer bag 3a for additional processing into platelet-poor plasma and platelet concentrate. The platelet-poor plasma is conveyed into integrally attached transfer bag 3b for storage. The platelet concentrate remains in transfer bag 3a for storage. The red blood cells are retained in the primary bag 2 for storage.

In conventional systems and procedures like that shown in FIG. 1, the donor tube 4 in which the whole blood samples are retained is integrally attached to the primary bag 2, where the cellular red blood cells are ultimately stored. Conventional blood collection systems and procedures therefore serve to preserve a direct link between the donor's whole blood samples and the separated cellular red blood cell components obtained from the donor.

In collecting whole blood components for transfusion, it is desirable to minimize the presence of impurities or other materials that may cause undesired side effects in the recipient. For example, because of possible febrile reactions, it is generally considered desirable to transfuse red blood cells substantially free of the white blood cell components, particularly for recipients who undergo frequent transfusions.

One way to remove white blood cells is by washing the red blood cells with saline. This technique is time consuming and inefficient, as it can reduce the number of red blood cells available for transfusion. The washing process also exposes the red blood cells to communication with the atmosphere, and thereby constitutes a "non-sterile" entry into the storage system. Once a non-sterile entry is made in a previously closed system, the system is considered "opened", and transfusion must occur within twenty-four hours, regardless of the manner in which the blood was collected and processed in the first place. In the United States, an entry into a blood collection system that presents the probability of non-sterility that exceeds one in a million is generally considered to constitute a "non-sterile" entry.

Another way to remove white blood cells is by filtration. Systems and methods for accomplishing this within the context of conventional multiple blood bag configurations are described in Wisdom U.S. Pat. Nos. 4,596,657 and 4,767,541, as well as in Carmen et al U.S. Pat. Nos. 4,810,378 and 4,855,063. In these arrangements, an inline white blood cell filtration device is used. In these arrangements, the red blood cells are transferred out of the primary bag for filtration. After filtration, the red blood cells, now substantially free of white blood cells, are retained in a separate transfer bag for storage.

In using these new systems and methods, it is still necessary to collect samples of the donor's whole blood in the donor tube for crossmatching and typing purposes. However, by transferring the red blood cells out of the original whole blood collection container (to which the donor tube is attached) into a another container for storage, these new systems and methods break the direct physical link that has heretofore existed between the red blood cell storage container and the donor tube, where the samples of the donor's whole blood are retained for analysis A need still exists for further improved systems and methods for removing undesired matter from blood components prior to transfusion or storage in a way that lends itself to use in closed multiple blood bag system environments and that assures accurate crossmatching and typing of cellular blood components prior to transfusion.

SUMMARY OF THE INVENTION

The invention provides methods and systems for collecting blood substantially free of undesired matter in a way that assures that accurate crossmatching and typing of cellular blood components can be done prior to transfusion.

In the systems and methods that embody the features of the invention, the blood containing the undesired matter is initially collected in a primary blood collection container. The primary collection container includes a tube that, in use, is sealed for retaining samples of the collected blood for later analysis. The systems and methods that embody the features of the invention convey the collected blood out of the primary container through a device that removes undesired matter from the blood. The blood, now substantially free of the undesired matter, is collected in a separate transfer container for storage.

According to the invention, at the time the blood is conveyed out of the primary container, a physical link is established between the sealed tube that contains the blood samples and the transfer container in which the blood is ultimately conveyed for storage. In the process, the systems and methods that embody the features of the invention sever the association between the sealed tube and the primary collection container, which no longer serves a long term storage function. According to the invention, the sealed tube and, with it, the retained blood sample, becomes associated only with the long term storage container for the blood, which is now substantially free of undesired matter.

Using the systems and methods that embody the features of the invention, direct traceability can be maintained between blood made substantially free of undesired matter for transfusion and the donor from whom the blood was originally obtained, despite the use of separate blood collection and blood storage containers.

Other features and advantages of the invention will become apparent upon review of the following description, drawings, and appended claims.

DESCRIPTION OF THE PREFERRED EMBODIMENTS

Figure 1:
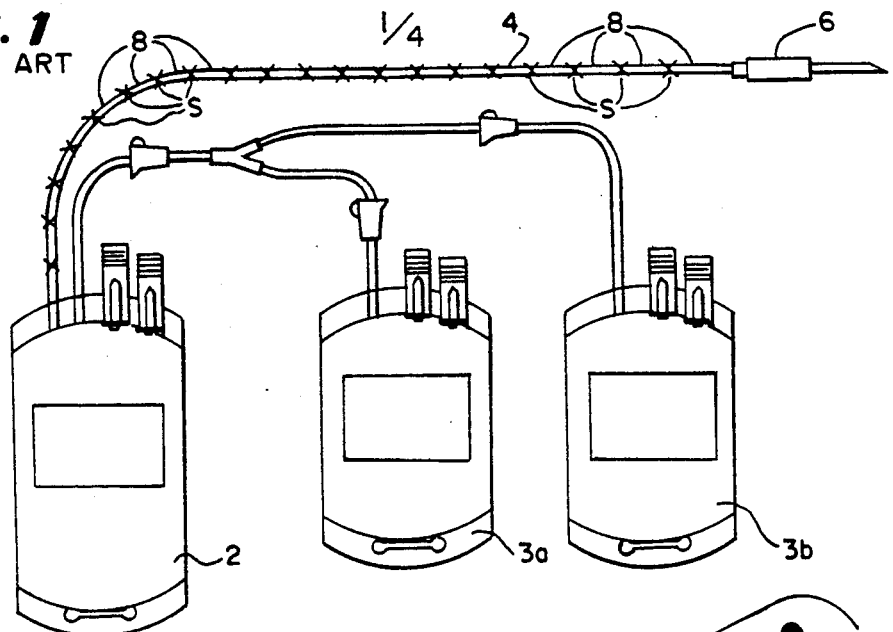
FIG. 1 is a schematic view of a conventional blood collection system.
Figure 2:
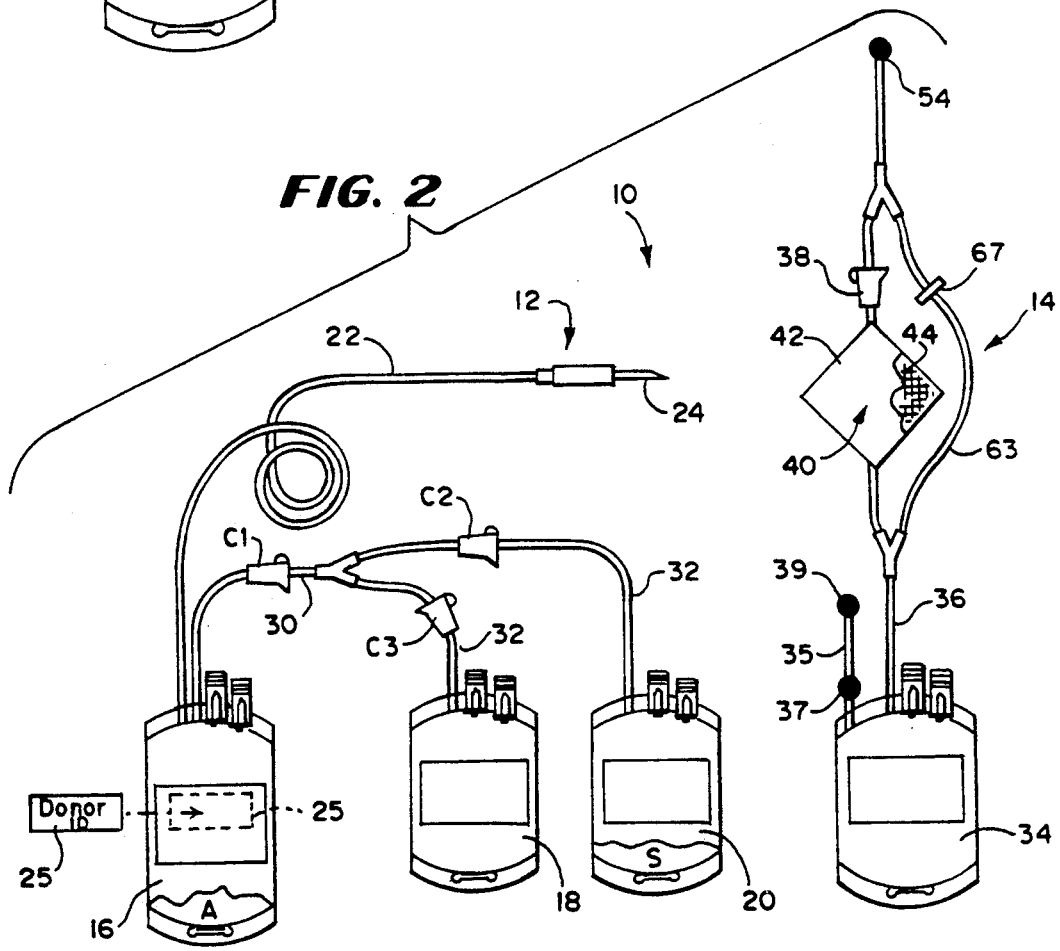
FIG. 2 is a schematic view of a blood collection system that includes a blood processing assembly and a blood filtration assembly that embody the features of the invention.

A blood Collection system 10 is shown in FIG. 2. The system 10 comprises a blood collection and processing assembly 12 and a separation and transfer assembly 14.

The blood collection and processing assembly 12 comprises a multiple blood bag system having a primary bag or container 16 and one or more integrally attached transfer bags or containers 18 and 20. In use, the primary bag 16 (which is typically also called a donor bag) receives whole blood from a donor through integrally attached donor tubing 22 by means of a phlebotomy needle 24. A suitable anticoagulant A is contained in the primary bag 16.

The transfer bags 18 and 20 are attached to the primary bag 16 by integrally attached transfer tubing 30 and 32. The transfer bags 18 and 20 are intended to receive the platelet and plasma blood components for processing. The first transfer bag 18 ultimately serves as the storage container for the platelet concentrate, and the second transfer bag 20 ultimately serves as the storage container for the platelet-poor plasma. Convention clamp devices C1, C2, and C3 control fluid flow through the associated transfer tubing 30, and 32, respectively.

The transfer bag 20 contains a suitable storage solution S for red blood cells. The storage solution S will ultimately be conveyed from the transfer bag 20 to the primary bag 16 during the course of blood processing.

A representative storage solution S is disclosed in Grode et al U.S. Pat. No. 4,267,269.

All of the bags and tubing associated with the processing assembly 12 can be made from conventional approved medical grade plastic materials, such as polyvinyl chloride plasticized with di-2-ethylhexylphthalate (DEHP). Alternatively, the first transfer container 18, which is intended to store the platelet concentrate, can be made of polyolefin material (as disclosed in Gajewski et al U.S. Pat. No. 4,140,162) or a polyvinyl chloride material plasticized with tri-2-ethylhexyl trimellitate (TEHTH). These materials, when compared to DEHP-plasticized polyvinyl chloride materials, have greater gas permeability that is beneficial for platelet storage.

The blood collection and storage assembly 12, once sterilized, constitutes a sterile, "closed" system, as judged by the applicable standards in the United States.

Whole blood is collected and then separated into its various therapeutic components within the assembly 12. These therapeutic components are typically red blood cells, plasma, and platelets. In the process of separating these components, a layer of white blood cells forms between the red blood cells and the platelet-rich plasma. This sequence of events is shown in FIG. 3.

After the desired amount of whole blood is collected from the donor, the phlebotomy needle 24 is removed from the donor. The phlebotomy needle 24 is then separated from the donor tube 22, while sealing the distal end 29 of the donor tube 22. A conventional heat sealing device (for example, the Hematron ® dielectric sealer sold by Baxter Healthcare Corporation) can be used for this purpose. The device forms a hermetic, snap-apart seal at the distal end 29 of the donor tubing 22 (this seal is schematically shown by an "x" in the drawings).

Next, the small amount of the collected whole blood that remains in the donor tubing 22 is pushed back into the primary bag 16, where it mixes with the anticoagulated whole blood. Anticoagulated whole blood is expressed out of the primary bag 16 back into the donor tube 22. A series of snap-apart seals "x" are formed along the length of the tube 22 using the heat sealing device. These seals form a series of snap-apart chambers 23, where discrete aliquots, or samples, of the donor's whole blood are retained for later analysis. In use, as will be described in greater detail later, one or more of the snap-apart chambers 23 are separated, and the retained blood samples are analyzed to crossmatch and type the donor's blood.

Figure 3:
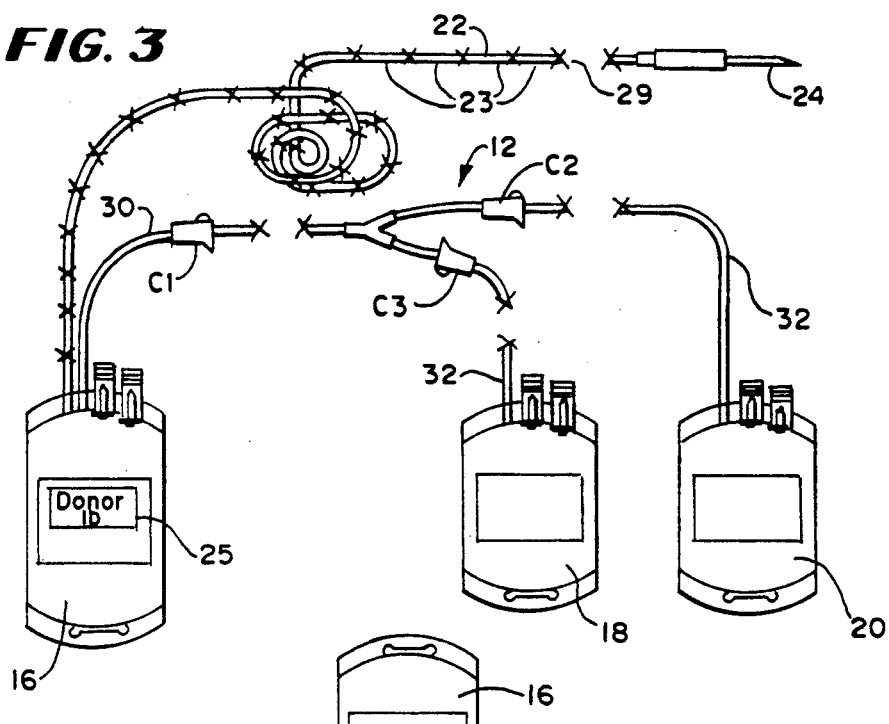
FIG. 3 is a schematic view of the blood processing assembly shown in FIG. 2 in use prior to its attachment to the blood filtration assembly.

Preferably (as FIGS. 2 and 3 show), before whole blood is collected, a removable donor-specific label 25 is attached to the blood collection container 16. The label 25 carries a unique identification number assigned to the particular donor at the time of donation.

The collected whole blood is next centrifugally separated within the primary bag 16 into red blood cells and platelet-rich plasma The layer of white blood cells forms between the red blood cells and the platelet rich plasma.

The platelet-rich plasma is transferred by conventional techniques into the first transfer bag 18, leaving the red blood cells and white blood cells in the primary bag 16. The red cell storage solution S is then transferred from the bag 20 to the primary bag 16 through the transfer tubing 30/32. The transfer bags 18 and 20 are detached as a unit using snap apart seals "x" formed by the heat sealing device.

The platelet-rich plasma undergoes subsequent centrifugal separation within the first transfer bag 18 into platelet concentrate and platelet-poor plasma. The platelet-poor plasma is transferred into the second transfer bag 20, leaving the platelet concentrate in the first transfer bag 18 The transfer bags 18 and 20 are then separated by snap-apart seals "x" formed in the tubing 32 for subsequent storage of the collected components.

As FIG. 2 shows, the filtration assembly 14 comprises an initially separate subassembly not joined to the blood processing assembly 12. The entire filtration assembly 14 is preferably provided in a "dry" condition, free of any fluids, storage mediums, and the like (except for any entrapped air), thereby avoiding regulatory requirements governing fluid-containing systems.

The filtration assembly 14 includes a transfer container 34 and an associated fluid flow path 36. The transfer container 34 also includes an integrally attached tubing segment 35 having closed proximal and distal ends 37 and 39.

The transfer container 34, fluid path 36, and closed tubing segment 35 are all made of low cost medical grade plastic materials, such as polyvinyl chloride plasticized with DEHP.

The fluid path 36 further includes an inline device 40 for separating undesired matter from blood cells.

In the illustrated embodiment, the separation assembly 14 serves to remove undesired matter from blood cells by filtration. For this reason, the device 40 will be referred to as a "filtration" device. It should be appreciated, however, that separation can occur by various centrifugal and non-centrifugal techniques, and not merely "filtration" in the technical sense. Separation can occur by absorption, columns, chemical, electrical, and electromagnetic means. The term "filtration device" is broadly used in this specification encompass all of these separation techniques as well.

It should be appreciated that the filtration assembly 14 can be used to remove all types of undesired materials from different types of blood cells, depending upon its particular construction In the illustrated embodiment, the filtration assembly 14 is intended to remove white blood cells (and preferably also platelets) from the red blood cells prior to storage.

In this arrangement, the filtration device 40 includes a housing 42 containing a conventional filtration medium 44 suited for the removal of white blood cells and platelets from red blood cells. The filtration medium 44 can include cotton wool, cellulose acetate or another synthetic fiber like polyester.

A conventional clamp 38 regulates flow through the fluid path 36 into the transfer container 34 via the filtration device 40.

Figure 4:
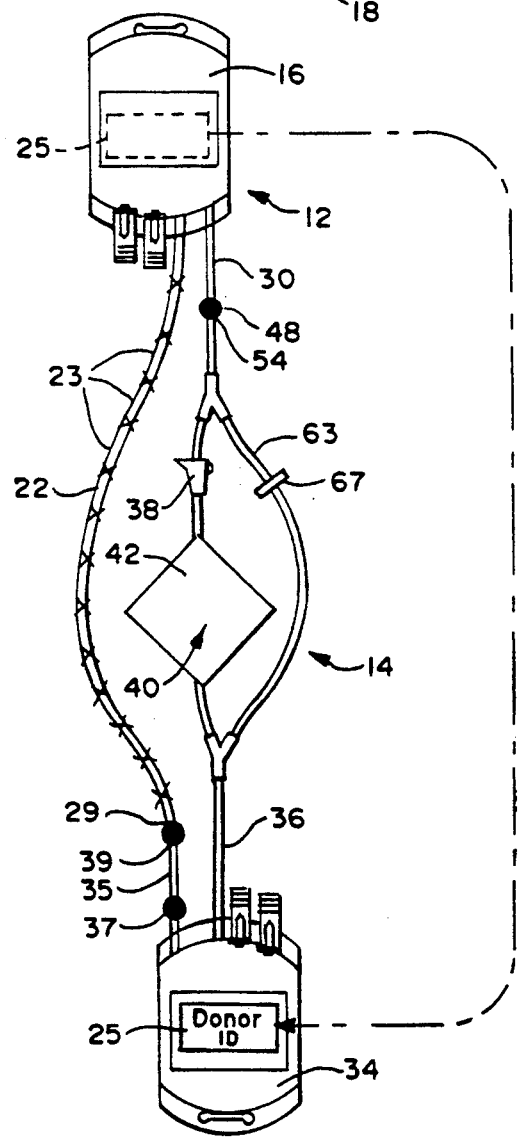
FIG. 4 is a schematic view of the blood processing assembly shown in FIG. 2 when attached to the blood filtration assembly for the purpose of removing undesired matter from the blood cells.

In the illustrated and preferred embodiment, a connection assembly 48 is associated with the initially separate blood collection and filtration assemblies 12 and 14. The connection assembly 48 permits selective attachment of the filtration assembly 14 to the blood collection assembly 12, as FIG. 4 shows.

In the illustrated and preferred embodiment, both assemblies 12 and 14, once sterilized, comprises sterile, "closed" systems, as judged by the applicable United States standards In this arrangement, the connection assembly 48 serves to attach the collection and filtration assemblies 12 and 14 in a manner that preserves the sterile integrity of the closed systems 12 and 14.

After removal of the platelet-rich plasma and addition of the storage solution S to the primary bag 16, the transfer bags 18 and 20 are detached from the assembly (as FIG. 3 shows). The donor bag 16 is attached to the filtration assembly 14 using the connection assembly 48 (as FIG. 4 shows).

The connection assembly 48 can be variously constructed It can comprise the sterile connecting system disclosed in Spencer U.S. Pat. No. 4,412,835 (not shown). In this arrangement (which is shown in FIG. 4), the system forms a molten seal between the transfer tubing 30 of the primary bag 16 with the tubing end portion 54 of the filtration assembly 14. Once cooled, a sterile weld is formed.

Figure 5:
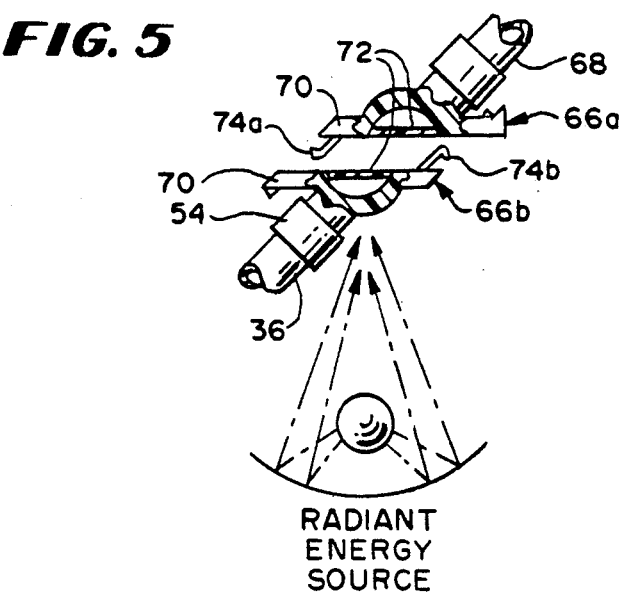
FIG. 5 is an enlarged side sectional view of a sterile connection assembly that can be associated with the system.
Figure 6:
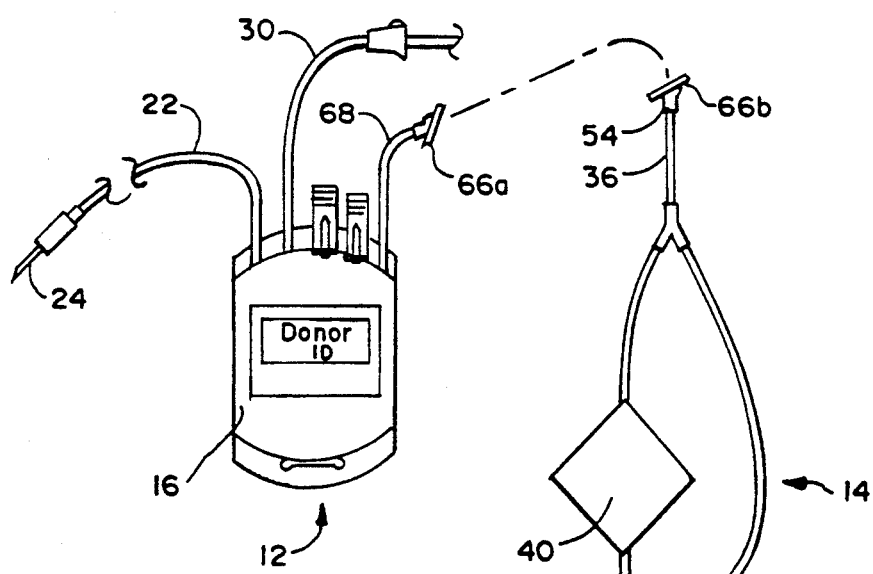
FIG. 6 is a schematic view of the system that incorporates the sterile connection assembly shown in FIG. 5.

In an alternate arrangement (which is shown in FIGS. 5 and 6), the connection assembly 48 comprises two mating sterile connection devices (designated 66a and 66b). The devices 66a and 66b (as FIG. 5 best shows) are described in Granzow et al U.S. Pat. Nos. 4,157,723 and 4,265,280, which are incorporated herein by reference In this arrangement, one device 66a is carried by tubing 68 attached to the primary bag 16. The other device 66b is carried at the tubing end 54 of the filtration assembly 14.

As shown in FIG. 5, the sterile connection devices 66a and 66b each generally includes a housing 70 having a normally closed, meltable wall 72 made of a radiant energy absorbing material. The housings 70 are joined together with mating bayonet-type couplers 74a and 74b, with the walls 72 placed in facing contact. When connected and exposed to radiant energy, the walls 72 melt at temperatures that result in the destruction of bacteria, while at the same time opening a fluid path between the connected housings 70.

The devices 66a and 66b normally close the associated assemblies 12 and 14 from communication with the atmosphere and are opened in conjunction with an active sterilization step which serves to sterilize the regions adjacent to the interconnecting fluid path as the fluid path is being formed. These devices 66a and 66b also hermetically seal the interconnecting fluid path at the time it is formed. The use of these sterile connection devices 66a and 66b assures a probability of non-sterility that exceeds one in a million. The devices 66a and 66b thus serve to connect the two assemblies 12 and 14 without compromising the sterile integrity of either.

According to the invention (as FIG. 4 shows), at the time the assemblies 12 and 14 are joined together, the closed distal end 29 of the donor tube 22 is also physically attached to transfer container 34, in which the red blood cells processed in the primary container 16 will ultimately be stored. In the illustrated embodiment, the attachment is made at the closed distal end 39 of the tubing segment 35.

As FIG. 4 shows, the closed tubing ends 29 and 37 can be permanently fused together using the sterile connecting system disclosed in Spencer U.S. Pat. No. 4,412,835. Alternatively, a manual clamping device (not shown) can join the two closed tubing ends 29 and 39 together.

In either case, the attachment is made without otherwise opening the assemblies 12 and 14 and the sample retaining chambers 23 to communication with the atmosphere.

Once these attachments are made, the flow clamp 38 is opened, and red blood cells are conveyed from the primary container 16 through the flow path 36 and filtration device 40 into the transfer container 34. In the process, the undesired white cells are removed by the filtration device 40 from the blood cells.

As shown in FIG. 4, the donor bag 16 is lifted above the transfer bag 34, and the red blood cells are conveyed by gravity flow from the donor bag 16 through the fluid path 36 and filtration device 40 and into the transfer bag 34.

Once the red blood cells are transferred, the donor-specific label 25 is removed from the primary bag 16 and applied to the transfer bag 34.

In the illustrated and preferred embodiment (shown in phantom lines in FIGS. 2 and 4), the transfer assembly 14 includes an air vent line 63 that provides an air venting path around the filtration device 40. A one way valve 67 controls fluid flow through the air vent line 63. The valve 67 does not allow passage of fluid in the direction of the transfer container 34. The valve 67 does allow passage of fluid in the opposite direction, away from the transfer container 34. Thus, should air be trapped in the transfer bag 34 in the process, the trapped air can be transferred out through the vent line 63 into the primary bag 16 through the one way valve 67 (while closing the clamp 38).

Figure 7:
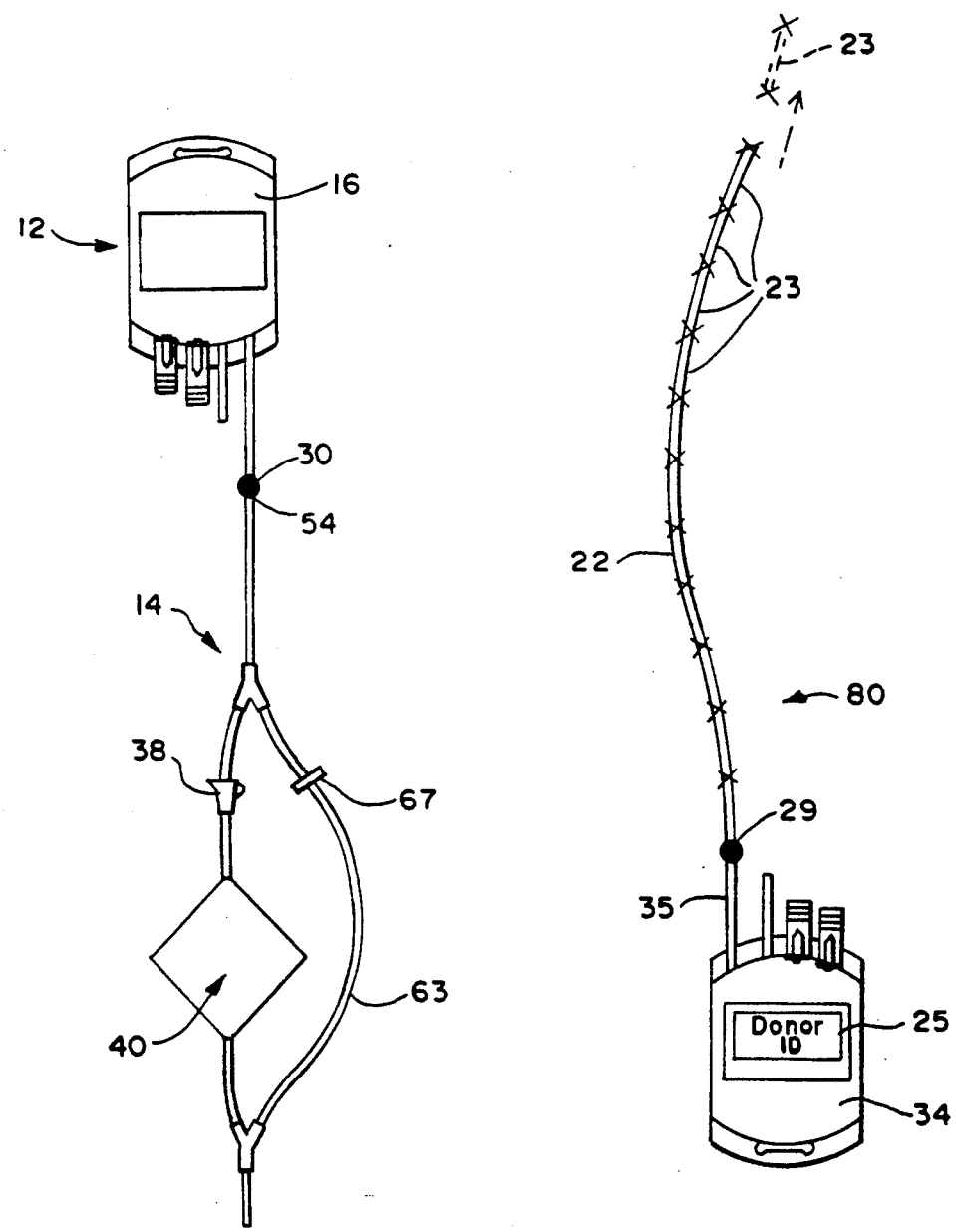
FIG. 7 is a schematic view of the system shown in FIG. 2, with the transfer container detached after filtration is completed for storing the filtered blood cells.

As FIG. 7 shows, the transfer bag 34 is then separated from the filtration assembly 14 and the joined processing assembly 12 by forming snap-apart seals "x" in the tubing between the bag 34 and the filtration device 40. At the same time, the donor tube 22 is separated from the primary bag 16 at the seal "x" closest to the primary bag 16. The connection formed between the closed tubing ends 29 and 39 secures the donor tube 22 (retaining the donor's original whole blood samples) to the transfer bag 34 independent of any association with the primary bag 16.

The resulting assembly 80 (shown in FIG. 7) comprises the transfer bag 34 to which the donor tube 22 retaining the samples of the donor's blood is secured. The transfer bag 34 also carries the donorspecific label 25.

The red blood cells, now substantially free of white blood cells, are stored in the transfer bag 34. The attached samples of the donor blood can be analyzed at a convenient time prior to transfusion for crossmatching and typing purposes by separating one or more of the snap-apart chambers 23 from the remaining donor tube 22 (shown by phantom lines in FIG. 7).

The invention assures direct traceability between the red blood cells made substantially free of white blood cells for transfusion and the donor from whom the red blood cells were obtained, while at the same time using separate blood processing container 12 and blood storage container 34.

Various features of the invention are set forth in the following claims.

We claim:

1. A method of collecting blood substantially free of undesired matter comprising the steps of
   collecting blood containing the undesired matter in a blood collection container that includes a tube having one end attached to the collection container and a free distal end,
   transferring a sample of the blood from the collection container into the attached tube through the distal end,
   sealing the distal end of the tube to retain the blood sample within the tube for subsequent analysis,
   attaching the sealed distal end of the tube to a transfer container that also includes attached transfer tubing that leads into the transfer container, the transfer tubing including means for separating undesired matter from the blood,
   opening communication between the blood collection container and the transfer tubing to convey at least a portion of the collected blood from the blood collection container into the transfer container through the separation means, thereby separating undesired matter from the blood,
   disconnecting the transfer container from the transfer tubing,
   sealing the disconnection adjacent to the transfer container to there close the transfer container, and
   disconnecting the other end of the sealed tube from the blood collection container leaving the sealed tube and, with it, the retained blood sample, attached only to the transfer container, which transfer container now holds blood substantially free of undesired matter.

2. A method according to claim 1
   and further including the step, which occurs after the step of separating the sealed tube from the blood collection container, of analyzing the blood sample retained within the tube.

3. A method according to claim 1
   and further including the step, which occurs after the step of disconnecting the transfer container, of storing the blood substantially free of undesired matter in the disconnected transfer container.

4. A method of collecting blood substantially free of undesired matter comprising the steps of collecting blood having the undesired matter into a blood collection container through collection tubing having one end attached to the blood collection container and a distal end that communicates with a source of the blood, disconnecting the distal end of the collection tubing from the blood source, closing the distal end of the collection tubing and conveying a sample of the collected blood into the collection tubing, closing the collection tubing adjacent to the blood collection container to retain the blood sample within the collection tubing for subsequent analysis, attaching the closed distal end of the collection tubing to a transfer container that includes attached transfer tubing that leads into the transfer container, the transfer tubing including means for separating undesired matter from the blood, opening communication between the blood collection container and the transfer tubing to convey at least a portion of the collected blood from the blood collection container into the transfer container through the separation means, thereby separating undesired matter from the blood, disconnecting the transfer container from the separation means, sealing the disconnection adjacent to the transfer container to there close the transfer container, and disconnecting the collection tubing from the blood collection container leaving the collection tubing and, with it, the retained blood sample attached only to the transfer container, which transfer container now holds blood substantially free of undesired matter.

5. A method according to claim 4 and further including the step, which occurs after the step of retaining the blood sample within the collection tubing, of separating the blood within the blood collection container into at least two component parts, wherein, in the step of conveying blood through the transfer tubing, one component part of the separated blood is conveyed into the transfer container through the separation means, and further including the step of conveying the other component part of the separated blood from the blood collection container through a fluid path that bypasses the separation means.

6. A method according to claim 4 and further including the step, which occurs after the step of separating the sealed tube from the blood collection container, of analyzing the blood sample retained within the tube.

7. A method according to claim 4 and further including the step of storing the blood substantially free of undesired matter in the disconnected transfer container.

8. A method according to claim 4 and further including the steps of attaching a removable source-specific label to the blood collection container before collecting blood therein, and after the steps of attaching the collection tubing holding the retained blood sample to the transfer container and conveying the blood from the blood collection container into the transfer container via the separation means, transferring the source-specific label from the blood collection container to the transfer container.

9. A method of collecting red blood cells substantially free of white blood cells comprising the steps of collecting whole blood into a blood collection container through a donor tube having one end attached to the blood collection container and a distal end that includes a phlebotomy needle in the blood donor, removing the phlebotomy needle from the blood donor, separating the phlebotomy needle while closing the distal end of the donor tube, conveying a sample of the collected whole blood into the donor tube and closing the donor tube adjacent to the blood collection container to retain the whole blood sample within the donor tube for subsequent analysis, separating the whole blood within the blood collection container into a layer of red blood cells, a layer of platelet-rich plasma, and an intermediate layer of white blood cells, conveying the platelet rich-plasma layer from the blood collection container into another container, attaching the closed distal end of the donor tube to a transfer container that includes an attached transfer tube that leads into the transfer container, the transfer tube including means for separating white blood cells from blood, opening communication between the blood collection container and the transfer tube to convey the red blood cells and white blood cells from the blood collection container through the separation means, thereby separating the white blood cells from the blood while conveying the red blood cells, now substantially free of white blood cells, into the transfer container, disconnecting the transfer container form the separation means, sealing the disconnection adjacent to the transfer container to there close the transfer container, and disconnecting the donor tube from the blood collection container leaving the donor tube and, with it, the retained whole blood sample attached only to the transfer container, which transfer container now holds red blood cells substantially free of undesired matter.

10. A method according to claim 9 and further including the step, which occurs after the step of separating the donor tube from the blood collection container, of analyzing the blood sample retained within the tube.

11. A method according to claim 9 and further including the step of storing the red blood cells substantially free of white blood cells in the disconnected transfer container.

12. A method according to claim 9 and further including the steps of attaching a removable donor-specific label to the blood collection container before collecting whole blood therein, and after the steps of attaching the donor tube holding the retained whole blood sample to the transfer container and conveying the red blood cells from the blood collection container into the transfer container via the separation means, transferring the donor-specific label from the blood collection container to the transfer container.

13. A blood processing system comprising
a blood collection assembly including
 a primary container,
 an inlet port for conveying blood into the primary container for collection,
 an outlet port for conveying collected blood from the primary container, and
 sample holding means communicating with the primary container for receiving and retaining for analysis a sample of the blood after collection in the primary container, and
a transfer assembly including
 a transfer container,
 a transfer path that communicates with the transfer container, the transfer path including means for separating undesired matter from blood,
 means for establishing communication between the outlet port of the primary container and the transfer path of the transfer container to convey blood from the primary container to the transfer container through the separation means, thereby removing undesired matter, and
 means carried by the transfer container to which the sample holding means of the primary container can be attached for securing the sample holding means to the transfer container free of association with the primary container and free of communication with the interior of the transfer container.

* * * * *